(12) United States Patent
Nzike et al.

(10) Patent No.: US 10,603,441 B2
(45) Date of Patent: Mar. 31, 2020

(54) WINDOW ELEMENT AND DRUG DELIVERY DEVICE

(71) Applicant: SANOFI-AVENTIS DEUTSCHLAND GMBH, Frankfurt am Main (DE)

(72) Inventors: Philippe Nzike, Frankfurt am Main (DE); Michael Schabbach, Frankfurt am Main (DE); Christian Pommerau, Frankfurt am Main (DE); Francisco Soares, Frankfurt am Main (DE)

(73) Assignee: Sanofi-Aventis Deutschland GMBH, Frankfurt am Main (DE)

( * ) Notice: Subject to any disclaimer, the term of this patent is extended or adjusted under 35 U.S.C. 154(b) by 417 days.

(21) Appl. No.: 15/518,388

(22) PCT Filed: Oct. 13, 2015

(86) PCT No.: PCT/EP2015/073607
§ 371 (c)(1),
(2) Date: Apr. 11, 2017

(87) PCT Pub. No.: WO2016/059010
PCT Pub. Date: Apr. 21, 2016

(65) Prior Publication Data
US 2017/0312442 A1    Nov. 2, 2017

(30) Foreign Application Priority Data

Oct. 16, 2014 (EP) ..................... 14189281

(51) Int. Cl.
*A61M 5/315* (2006.01)
*G06M 1/22* (2006.01)
(Continued)

(52) U.S. Cl.
CPC .... *A61M 5/31551* (2013.01); *A61M 5/31585* (2013.01); *A61M 5/31593* (2013.01);
(Continued)

(58) Field of Classification Search
CPC .......... A61M 5/31551; A61M 5/31585; A61M 5/31593; A61M 2205/581;
(Continued)

(56) References Cited

U.S. PATENT DOCUMENTS 2,586,581 A    2/1952  Tschischeck
4,178,071 A *  12/1979 Asbell ................. A61M 5/3129
                                                 359/442
(Continued)

FOREIGN PATENT DOCUMENTS

CN    201402346    2/2010
DE    202008011175  1/2010
(Continued)

OTHER PUBLICATIONS

International Preliminary Report on Patentability in International Application No. PCT/EP2015/073607, dated Apr. 18, 2017, 9 pages.
(Continued)

*Primary Examiner* — Nathan R Price
*Assistant Examiner* — Tasnim Mehjabin Ahmed
(74) *Attorney, Agent, or Firm* — Fish & Richardson P.C.

(57) ABSTRACT

The present disclosure is directed to a window element and a drug delivery device, like a pen-type injector, that provides for administration by injection of medicinal products from a multidose cartridge. The drug delivery device may comprise a housing, a dose setting member, a dial, a drive member, a clutch and/or a clicker. The window element comprises a first member with a window and being made from a rigid material, a second member and a third member, each made from an elastically deformable material and being attached to the first member.

15 Claims, 1 Drawing Sheet

(51) Int. Cl.
*A61M 5/31* (2006.01)
*A61M 5/14* (2006.01)
*G06M 1/02* (2006.01)

(52) U.S. Cl.
CPC ............... *G06M 1/22* (2013.01); *A61M 5/14* (2013.01); *A61M 2005/3126* (2013.01); *A61M 2205/0216* (2013.01); *A61M 2205/581* (2013.01); *A61M 2205/582* (2013.01); *A61M 2205/585* (2013.01); *A61M 2205/586* (2013.01); *G06M 1/02* (2013.01)

(58) Field of Classification Search
CPC ...... A61M 2205/582; A61M 2205/585; A61M 2205/586
See application file for complete search history.

(56) References Cited

U.S. PATENT DOCUMENTS 6,081,392 A * 6/2000 Pensmith ............. G02B 25/002
359/440
2010/0168677 A1 * 7/2010 Gabriel ............. A61M 5/31551
604/189
2010/0274198 A1 * 10/2010 Bechtold ........... A61M 5/31551
604/189
2014/0268373 A1 9/2014 Selness

FOREIGN PATENT DOCUMENTS

| JP | 2012-500067 | 1/2012 |
|---|---|---|
| WO | WO 96/26754 | 9/1996 |
| WO | WO 2010/020311 | 2/2010 |
| WO | WO 2013/070705 | 5/2013 |
| WO | WO 2013/149980 | 10/2013 |

OTHER PUBLICATIONS

International Search Report and Written Opinion in International Application No. PCT/EP2015/073607, dated Feb. 1, 2016, 11 pages.

* cited by examiner

WINDOW ELEMENT AND DRUG DELIVERY DEVICE

CROSS-REFERENCE TO RELATED APPLICATIONS

This application is a U.S. national stage application under 35 USC § 371 of International Application No. PCT/EP2015/073607, filed on Oct. 13, 2015, which claims priority to European Patent Application No. 14189281.0 filed on Oct. 16, 2014, the entire contents of which are incorporated herein by reference.

TECHNICAL FIELD

The present invention is directed to a window element and a drug delivery device, like a pen-type injector, that provides for administration by injection of medicinal products from a multidose cartridge. The drug delivery device may comprise a housing, a dose setting member, a dial (number sleeve), a drive member (drive sleeve), a clutch and/or a clicker.

BACKGROUND

One important feature of known drug delivery devices is to provide means allowing a user to identify the dose selected and/or administered. For this purpose, known devices comprise a dial or number sleeve having numbers, letters or signs on its outer surface which are at least partly visible through the housing, e.g. a window in the housing. In some known devices the dial or number sleeve rotates during dose setting and/or during dose dispense, wherein only one single number, letter or sign corresponding to the selected dose is visible through the window. An example of such a known drug delivery devices is described in WO 2008/145171 A1.

Further DE 20 2008 011 175 U1 and WO 2010/020311 A1 disclose a similar mechanism having a housing with a housing wall and a first window provided in the same. A dial is rotatably disposed in the housing, on which dosing values are disposed in a spiral shape and are partially visible through the first window. A second window is located in the housing and is disposed displaceably in the longitudinal axis of the housing, wherein a rotational motion of the dial is synchronized with a longitudinal displacement of the second window, in order to display the currently set injection dosage through the first window and the second window. A first transparent lens arrangement is located in the first window, said arrangement acting on its own to distort the display values visible there through. A second lens arrangement is located in the second window, said arrangement acting together with the first lens arrangement to increase the legibility of a set dosage value visible through the first lens arrangement and the second lens arrangement, and thereby counteracting false readings of the selected dosage setting.

Although the first transparent lens arrangement distorts the display values visible there through, the values may still be seen which might confuse the user. In addition, the arrangement with different lenses which have to match with each other to allow only one dose value to be visible is complicated.

SUMMARY

Certain aspects of this disclosure provide an improved window element and a drug delivery device that decreases the danger of malfunction.

A window element according to the present disclosure comprises a first member with a window and is made from a rigid material. The window element further comprises a second member and a third member, each made from an elastically deformable, flexible material and being attached to the first member. The terms "rigid" and "elastically deformable" describe the different material properties of the first member on the one hand and the second and third member on the other hand. The rigidity of the first member is much higher than the rigidity of the second and third member. Further, the ability to be elastically deformed is much higher for the second and third member compared with the first member. As an example, the first member may be made from a stiff plastic material whereas the second and third member may be made from a rubber-like material which can be easily compressed and/or stretched. In other words, the second and third member act like a spring suspension or bellows for the first member which is located between the second and third member. For example, the second and third member may be fixed to a housing or the like stationary component part, while the first member is movable with respect thereto. Attachment of the second and third member may include a pin of the housing engaging a hole in the second or third member or gluing or welding the second and third member to the housing.

According to a preferred embodiment of the disclosure the window in the first member is defined by a transparent or translucent element. In addition, the window in the first member may comprise a magnifying lens. As an alternative, the window in the first member may be defined by a frame surrounding an opening. In contrast to the window, the further parts of the window element, especially the second and third member, are made from an opaque material preventing a user to see through this material.

Typically, the movement of the first member is an axial movement. Thus, the first member preferably comprises guiding means for guiding the window in an axial track or a flute. The guiding means may comprise guiding bars, guiding slots or rails.

To generate a movement of the first member coupling means may be provided for attaching and/or entraining the window. Suitable coupling means may include a tappet or an attachment to a further element. In a preferred embodiment, the first member is in threaded engagement with a thread of a corresponding element which is rotated and/or axially moved e.g. during dose setting. For example, the first member may engage a threaded dial or lead screw.

According to a preferred embodiment of the present disclosure the first member is displaceable relative to at least a part of the second member and/or a part of the third member by compressing one of the second member and the third member and simultaneously stretching the other of the second member and the third member.

In addition, the window element may further comprise a fourth member and a fifth member each made from a rigid material, e.g. a material with similar material properties like the first member but not necessarily transparent or translucent, wherein the fourth member and the fifth member are attached to the second member and the third member, respectively, at a side facing away from the first member. According to a further development of this idea, the fourth member and the fifth member each comprise coupling means for attaching the fourth member and the fifth member such that the first member is movable relative to the fourth member and the fifth member. In other words, the fourth member and the fifth member form a fixed or locating bearing with the first member movable between the fourth member and the fifth member by the resilient material properties of the second and third member.

The present disclosure further relates to a drug delivery device comprising a housing and a window element as defined above, wherein the first member of the window element is displaceable relative to the housing. Thus, the window element may be used to disclose only a single number, letter or sign of a series of multiple numbers, letters or signs to a user by moving the window over the respective single number, letter or sign. Preferably, the single number, letter or sign is associated to a certain dose of the drug delivery device.

In a preferred arrangement of the drug delivery device according to the disclosure the fourth member and the fifth member of the window element are fixed to the housing and the first member of the window element is guided in the housing in a slidable manner. For this purpose, the housing may comprise an axial track or a flute in which the guiding means of the first member of the window element is guided.

It is preferred if the drug delivery device further comprises a drive mechanism received at least in part within the housing. At least one component of the drive mechanism, which component performs an axial, rotational or helical movement during dose setting and/or dose dispensing, may be coupled to the coupling means of the first member of the window element. Thus, said component may be used to entrain or drive the window and the first member.

According to a further development of this idea, the drug delivery device further comprises a dial, e.g. a number sleeve, which is at least partly received within the housing and which is rotatable relative to the housing during dose setting and/or dose dispensing, wherein the window element and the dial are arranged such that at least a part of the dial is visible through the window in the first member of the window element. The dial may have on its outer surface a series of multiple numbers, letters or signs each indicating a certain dose value. The series of multiple numbers, letters or signs may be arranged along a helical path, i.e. in spiral shape, on the dial.

It is preferred if the window in the first member of the window element is disposed displaceably in the longitudinal axis of the housing, wherein a rotational motion of the dial is synchronized with a longitudinal displacement of the window, in order to display the currently set injection dose through the window.

In addition to the visible indication of a set dose, it is preferred to produce a tactile and audible feedback to a user. For this purpose, it is preferred to provide a clicker.

A further independent aspect of the present disclosure refers to a clicker for producing a tactile and/or audible feedback to a user during operation of a drug delivery device. In more detail, the clicker may comprise a first component part and a second component part which perform a relative rotation during operation of the device. For example, a number sleeve may rotate relative to a clutch, e.g. during dose setting, dose correcting and/or dose dispensing. According to the present disclosure, the first component part comprises at least one recess, like a groove, or protrusion, like a tooth, while the second component part houses at least one pin, which is movable in a direction perpendicular to the axis of rotation of the first and/or second component part. Preferably, the at least one pin is biased by a spring or the like flexible member towards the recess or protrusion. In other words, the pin engages and disengages the recess or protrusion as the two component parts rotate relative to each other. This generates a tactile and/or audible feedback. In a preferred embodiment the clicker comprises a clutch sleeve with a series of radially facing teeth and a number sleeve housing a series of pins, which are spring biased in a radial direction towards the teeth of the clutch sleeve. During operation of the clicker, the pins oscillate as they ride over the teeth during a relative rotation of the clutch sleeve and the number sleeve.

In the following, the disclosure will be described by a way of an example and with reference to the schematic drawings. Those skilled in the art will understand, however, that changes and modifications may be made to these embodiments without departing from the true scope and spirit of the presently proposed device, which is defined by the claims. The disclosure is not limited to the embodiment described in the following and each feature forms a basis of the present disclosure independent from the further features and irrespective of the description in the exemplary embodiment.

DETAILED DESCRIPTION

Figure 1:
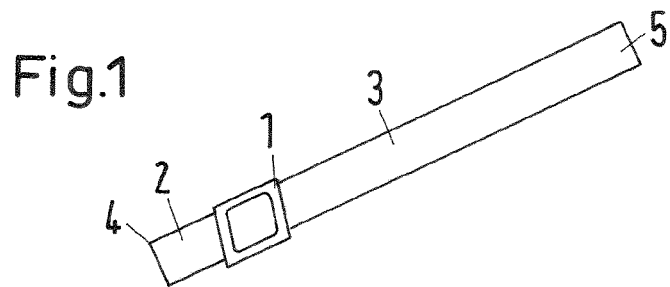
FIG. 1 shows a window element according to the disclosure.

FIG. 1 depicts a window element which may be used in the housing of a drug delivery device. The window element has a first member 1 which comprises a window formed by a frame and a magnifying lens. The first member 1 is made from a transparent, relatively stiff plastic material. On two opposite sides of the first member 1, there are provided respectively a second member 2 and a third member 3 which are made from an elastically deformable material, especially a rubber-like material. The second member 2 and the third member 3 are permanently attached to the first member 1. Further, the second member 2 is provided with a fourth member 4 at the side facing away from the first member 1. In a similar manner, the third member 3 is provided with a fifth member 5 on its side facing away from the first member 1. The fourth member 4 and the fifth member 5 are made from a stiff or rigid material. The material of the second, third, fourth and fifth member is opaque, i.e. not transparent.

Due to the elastic material properties of the second and third member, the first member 1 may be displaced relative to the fourth member 4 and the fifth member 5 by compressing or stretching the second or third member. In other words, the fourth member 4 and the fifth member 5 may form a fixed or locating bearing with the first member being displaceably suspended between the fourth and fifth member.

FIGS. 2 to 5 depict a drug delivery device in the form of an injection pen. In the embodiment shown, the drug delivery device comprises a cartridge holder 6 for receiving an ampoule or cartridge containing a medicament and attaching same to a housing 7 of the drug delivery device. Further, a dose setting member 8 is provided which is rotatable relative to the housing 7 to set or correct a dose. A button 9 is provided to administer the dose set by the dose setting member 8. The dose setting member 8 and the button 9 may be part of a drive mechanism which is shown in more detail in FIG. 5.

The drive mechanism further comprises a dial 10 which may have the form of a number sleeve having at its outer surface a series of numbers 10a, 10b, 10c which may be arranged on a helical path. During dose setting and dose dispensing dial 10 is rotated within the housing 7. As can be seen from FIGS. 2, 3 and 4 the window element of FIG. 1 is attached to or assembled into the housing 7. The fourth member 4 and the fifth member 5 are fixed within the housing 7 and the first member 1 is guided within an axial track in the housing 7. Thus, the first member 1 may be moved along an axial path relative to the housing 7 and the fourth and fifth members by compressing and stretching the flexible second member 2 and third member 3, respectively. The first member 1 with its window is further coupled to dial 10, which preferably surrounds dose setting member 8, with the first member 1 being in threaded engagement with dial 10. Dose setting member 8 may entrain or drive dial 10 during operation of the device.

Figure 2:
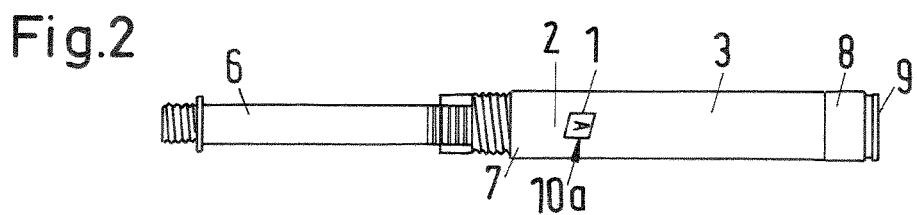
FIG. 2 shows a side view on a drug delivery device according to the disclosure in a first state.
Figure 3:
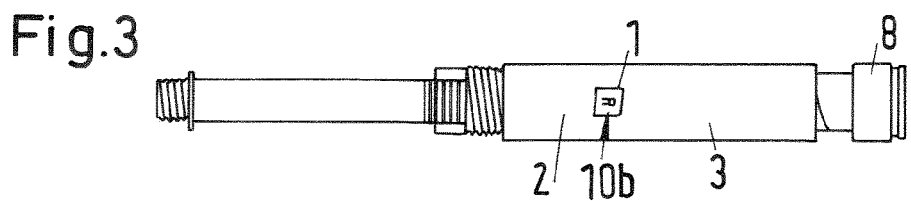
FIG. 3 shows a side view on the drug delivery device of FIG. 2 in a second state.
Figure 4:
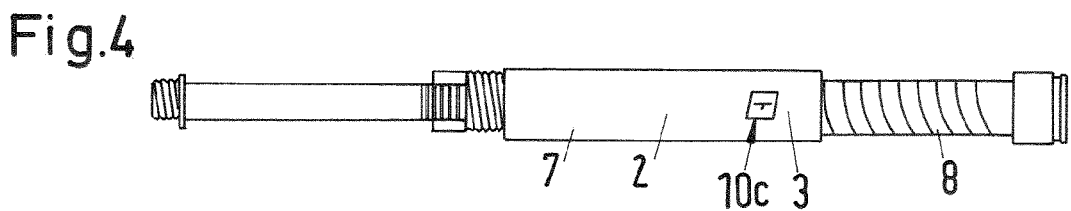
FIG. 4 shows a side view on the drug delivery device of FIG. 2 in a third state.

To set a dose, a user rotates the dose setting member 8 relative to the housing 7 in a clockwise direction. As the dose setting member 8 is in a threaded engagement with the housing 7, the dose setting member 8 is screwed out of the housing 7. FIG. 2 shows an initial state of the drug delivery device where the set dose is zero. In FIG. 3, a small dose has been selected by winding dose setting member 8 out of the housing 7. FIG. 4 shows the state of the drug delivery device where the maximum dose has been set.

Upon rotation of the dose setting member 8 dial 10 is rotated, too, by way of a coupling not shown in further detail. However, dial 10 is axially fixed within housing 7 such that it does not wind out of the housing 7. Due to the coupling between the first member 1 and the dose setting member 8, the window of the first element 1 follows the axial movement of the dose setting member 8 such that different numbers 10a, 10b, 10c, respectively, are visible through the window in the first element 1.

In the state of FIG. 2, the second member 2 of the window element is fully compressed whereas the third member is stretched. In contrast to that, the state shown in FIG. 4, where maximum dose has been set, shows the second member 2 fully stretched and the third member 3 fully compressed. Thus, the slot or opening in the housing 7 where the window element is received, is in any state of the drug delivery device closed to the outside to prevent dirt or the like entering the device.

In addition, only one single number which represents the presently set dose of the drug delivery device is visible through the window in the first member whereas the other numbers on dial 10 are concealed or masked by the housing 7 and the second member 2 and the third member 3.

During dose injection the user pushes button 9 which causes the dose setting member 8 to rewind into housing 7 until the state shown in FIG. 2. At the same time, dial 10 is rotated back and the first member 1 slides back to the position shown in FIG. 2. Pushing button 9 further causes the drive mechanism to entrain or push a piston rod farther into the cartridge to expel the selected dose of a medicament from the cartridge.

Figure 5:
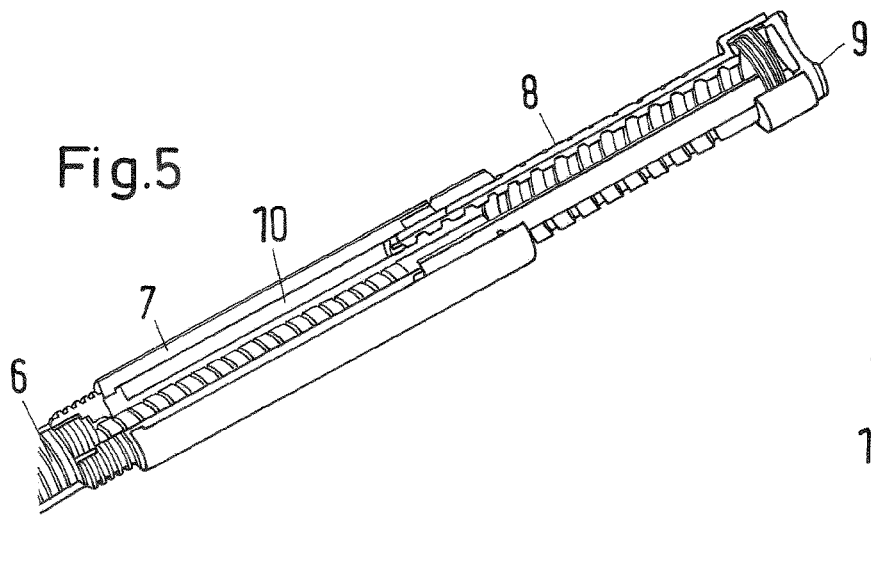
FIG. 5 shows a sectional view on the drug delivery device of FIG. 2.
Figure 6:
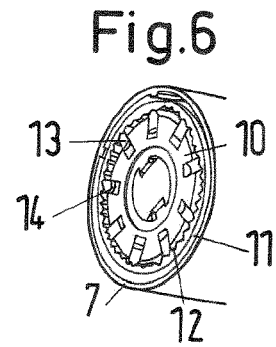
FIG. 6 shows a sectional view of a clicker according to the disclosure.

FIG. 6 shows in a sectional view the device of FIG. 5 with housing 7 and dial 10. Further, a clutch 11 is provided having a series of inwardly directed teeth 12 located at its inner surface. The dial 10 comprises bores or slots in which pins 13 are guided to allow movement of the pins in a radial direction, i.e. towards the teeth 12. Each bore or slot further houses a spring 14 acting on the respective pin 13 to bias the pin towards the teeth 12. In operation of the device, e.g. during dose setting and/or dose dispensing, dial 10 rotates relative to clutch 11, thus generating a feedback signal by the pins 13 riding over teeth 12. In an alternative embodiment, the pins 13 may be guided within clutch sleeve 11, while the dial 10 comprises the teeth 12.

The term "medicament", as used herein, means a pharmaceutical formulation containing at least one pharmaceutically active compound, wherein in one embodiment the pharmaceutically active compound has a molecular weight up to 1500 Da and/or is a peptide, a protein, a polysaccharide, a vaccine, a DNA, a RNA, an enzyme, an antibody or a fragment thereof, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exendin-3 or exendin-4 or an analogue or derivative of exendin-3 or exendin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des (B30) human insulin; B29-N-palmitoyl-des (B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2.

Exendin-4 derivatives are for example selected from the following list of compounds:

H-(Lys)4-des Pro36, des Pro37 Exendin-4(1-39)-NH2,
H-(Lys)5-des Pro36, des Pro37 Exendin-4(1-39)-NH2,
des Pro36 Exendin-4(1-39),
des Pro36 [Asp28] Exendin-4(1-39), des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4 (1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4 (1-39),
wherein the group -Lys6-NH2 may be bound to the C-terminus of the Exendin-4 derivative;
or an Exendin-4 derivative of the sequence
des Pro36 Exendin-4(1-39)-Lys6-NH2 (AVE0010),
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4(1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4(1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4(1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4 (1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2,
H-(Lys)6-desPro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4 (1-39)-(Lys)6-NH2,
H-(Lys)6-des Pro36, Pro37, Pro38 [Met(O)14, Asp28] Exendin-4(1-39)-(Lys)6-NH2,
H-Asn-(Glu)5 des Pro36, Pro37, Pro38 [Met(O)14, Asp28] Exendin-4(1-39)-(Lys)6-NH2,
H-Lys6-des Pro36 [Met(O)14, Trp(O2)25, Asp28] Exendin-4(1-39)-Lys6-NH2,
H-des Asp28 Pro36, Pro37, Pro38 [Met(O)14, Trp(O2)25] Exendin-4(1-39)-NH2,
H-(Lys)6-des Pro36, Pro37, Pro38 [Met(O)14, Asp28] Exendin-4(1-39)-NH2,
H-Asn-(Glu)5-des Pro36, Pro37, Pro38 [Met(O)14, Trp (O2)25, Asp28] Exendin-4(1-39)-NH2,
des Pro36, Pro37, Pro38 [Met(O)14, Trp(O2)25, Asp28] Exendin-4(1-39)-(Lys)6-NH2,
H-(Lys)6-des Pro36, Pro37, Pro38 [Met(O)14, Trp(O2) 25, Asp28] Exendin-4(S1-39)-(Lys)6-NH2,
H-Asn-(Glu)5-des Pro36, Pro37, Pro38 [Met(O)14, Trp (O2)25, Asp28] Exendin-4(1-39)-(Lys)6-NH2;
or a pharmaceutically acceptable salt or solvate of any one of the afore-mentioned Exendin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Antibodies are globular plasma proteins (~150 kDa) that are also known as immunoglobulins which share a basic structure. As they have sugar chains added to amino acid residues, they are glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two β sheets create a "sandwich" shape, held together by interactions between conserved cysteines and other charged amino acids.

There are five types of mammalian Ig heavy chain denoted by α, δ, ε, γ, and μ. The type of heavy chain present defines the isotype of antibody; these chains are found in IgA, IgD, IgE, IgG, and IgM antibodies, respectively.

Distinct heavy chains differ in size and composition; α and γ contain approximately 450 amino acids and approximately 500 amino acids, while μ and ε have approximately 550 amino acids. Each heavy chain has two regions, the constant region (CH) and the variable region (VH). In one species, the constant region is essentially identical in all antibodies of the same isotype, but differs in antibodies of different isotypes. Heavy chains γ, α and δ have a constant region composed of three tandem Ig domains, and a hinge region for added flexibility; heavy chains μ and E have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by λ and κ. A light chain has two successive domains: one constant domain (CL) and one variable domain (VL). The approximate length of a light chain is 211 to 217 amino acids. Each antibody contains two light chains that are always identical; only one type of light chain, κ or λ, is present per antibody in mammals.

Although the general structure of all antibodies is very similar, the unique property of a given antibody is determined by the variable (V) regions, as detailed above. More specifically, variable loops, three each the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antibody fragment" contains at least one antigen binding fragment as defined above, and exhibits essentially the same function and specificity as the complete antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystalizable fragment (Fc). The Fc contains carbohydrates, complement-binding, and FcR-binding sites. Limited pepsin digestion yields a single F(ab')2 fragment containing both Fab pieces and the hinge region, including the H—H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

The invention claimed is:

1. A drug delivery device comprising:
    a housing; and
    a window element, wherein the window element comprises:
        a first member comprising a window disposed in the housing and configured to be displaced along a longitudinal axis of the housing, wherein the first member is rigid,
        a second member,
        a third member, each of the second and third members being elastically deformable and being attached to the first member, and
        a dial at least partly received within the housing and rotatable relative to the housing during dose setting or dose dispensing,
    wherein the window element and the dial are arranged such that at least a part of the dial is visible through the window of the first member, wherein a rotational motion of the dial is synchronized with a longitudinal displacement of the window of the first member, and wherein the first member is displaceable relative to at least a part of the second member or a part of the third member by compressing one of the second member and the third member and simultaneously stretching the other of the second member and the third member.

2. The drug delivery device according to claim 1, wherein the window of the first member is a transparent or translucent element.

3. The drug delivery device according to claim 1, wherein the window of the first member comprises a magnifying lens.

4. The drug delivery device according to claim 1, wherein the window of the first member comprises a frame surrounding an opening.

5. The drug delivery device according to claim 1, wherein the first member comprises a guiding element configured to guide the window in an axial track or a flute.

6. The drug delivery device according to claim 1, wherein the first member comprises a coupling element configured to attach to or entrain the window.

7. The drug delivery device according to claim 1, comprising a fourth member and a fifth member, wherein each of the fourth and fifth members is rigid, and wherein the fourth member and the fifth member are attached to the second member and the third member, respectively, at a respective side of the second and third members facing away from the first member.

8. The drug delivery device according to claim 7, wherein the fourth member and the fifth member each comprise a coupling element configured to attach the fourth member and the fifth member to the second and third members, respectively, such that the first member is movable relative to the fourth member and the fifth member.

9. The drug delivery device according to claim 7, wherein the fourth member and the fifth member are fixed to the housing, and the first member comprises a guiding element configured to guide the window in the housing in a slidable manner.

10. The drug delivery device according to claim 9, wherein the housing comprises an axial track or a flute in which the guiding element of the first member is guided.

11. The drug delivery device according to claim 1, comprising a drive mechanism received at least in part within the housing, wherein at least one component of the drive mechanism is coupled to a coupling element of the first member, and wherein the at least one component of the drive mechanism performs one or more of: an axial movement, a rotational movement, and a helical movement during dose setting and/or dose dispensing.

12. The drug delivery device according to claim 1, comprising a first component part with at least one tooth and a second component part configured to perform a relative rotation during operation of the device, wherein the second component part houses at least one pin, which is movable in a direction perpendicular to an axis of rotation of the first and/or second component part.

13. The drug delivery device according to claim 12, wherein the second component part comprises at least one flexible member biasing the at least one pin towards the at least one tooth.

14. The drug delivery device of claim 1 comprising a cartridge containing a medicament, wherein the drug delivery device comprises a piston in the housing configured to expel a dose of the medicament from the cartridge.

15. The drug delivery device of claim 14, wherein the medicament comprises a pharmaceutically active compound.

* * * * *